United States Patent [19]

Matsunaga et al.

[11] 4,022,768
[45] May 10, 1977

[54] PROCESS FOR PREPARATION OF 1α,25-DIHYDROXYCHOLECALCIFEROL

[75] Inventors: Isao Matsunaga, Tokyo; Kiyoshige Ochi, Kawagoe; Hiroyuki Nagano, Ageo; Minoru Shindo, Higashikurume; Masayuki Ishikawa; Chikara Kaneko, both of Tokyo, all of Japan; Hector F. DeLuca, Madison, Wis.

[73] Assignee: Wisconsin Alumni Research Foundation, Madison, Wis.

[22] Filed: Feb. 12, 1976

[21] Appl. No.: 657,375

[52] U.S. Cl. ............................ 260/239.5; 260/397.2
[51] Int. Cl.² ........................................ C07J 71/00
[58] Field of Search ...................... 260/397.2, 239.5

[56] References Cited
UNITED STATES PATENTS 3,929,770  12/1975  Ishikawa et al. ............... 260/397.2

Primary Examiner—Elbert L. Roberts
Attorney, Agent, or Firm—Howard W. Bremer

[57] ABSTRACT

1α,25-dihydroxycholecalciferol is prepared by reacting 1,5,7-trien-3β,25-diol with a 1,2,4-triazoline-dione derivative represented by the formula:

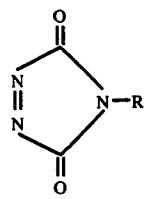

wherein R represents an alkyl group or an aryl or substituted-aryl group; reacting the resulting 1,4-cyclic adduct represented by the general formula

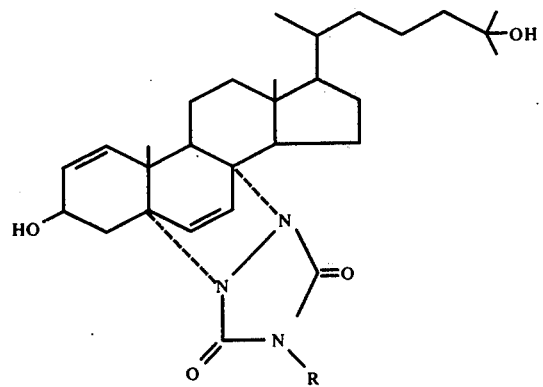

wherein R is as defined above, with a peroxide to form a 1α,2α-epoxide compound represented by the general formula

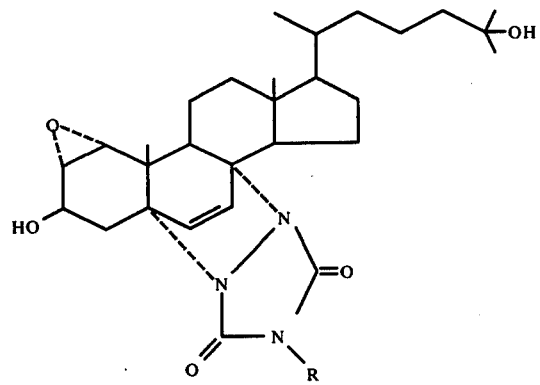

wherein R is as defined above, reducing the so formed compound with a metal hydride to form cholesta-5,7-diene-1α,3β,25-triol, irradiating the so formed compound with ultraviolet rays to form 1α,25-dihydroxyprevitamin D₃, isomerizing the so formed previtamin D₃, and recovering 1α,25-dihydroxycholecalciferol.

5 Claims, No Drawings

PROCESS FOR PREPARATION OF 1α,25-DIHYDROXYCHOLECALCIFEROL

This invention relates to a novel process for the preparation of 1α,25-dihydroxycholeclaciferol, a compound exhibiting greater activity than vitamins $D_2$ and $D_3$ as measured by its antirachitic properties, and which has value as a nutritional adjuvant, and to intermediates used for preparing the same.

Processes for preparing 1α,25-dihydroxycholecalciferol have heretofore been known (see DeLuca et al., Tetrahedron Letters, page 4147 (1972) and Barton et al., J. Chem. Soc. Chem. Comm., page 203 (1974)). Each of these known processes passes through a triacyl derivative of 1α,25-dihydroxyprovitamin $D_3$ as an intermediate, and in order to form the 5,7-diene system in this intermediate, such severe reactions as introduction of a bromine atom into the 7-position and dehydrobromination must be conducted. Accordingly, in these known processes, hydroxy groups at the 1α-, 3β- and 25-positions should be protected with an acyl group or the like, and the protective groups should naturally be removed in subsequent steps. A series of such severe reactions as introduction of a bromine atom into the 7-position and dehydrobromination and removal of acyl groups causes formation of various by-products. Consequently, complicated purification means must be adopted and the yield is inevitably lowered. This is particularly true with the process of Barton et al, since the process passes through 1α,2α-epoxycholesta-4,6-dien-3-one-25-ol as an intermediate, requiring a very dangerous Birch reduction (using liquid ammonia-metallic lithium) and such a cumbersome purification process as preparative TLC, several times in the process steps. Accordingly, each of these known processes cannot be considered to be an industrially practical process.

The process of this invention provides a method for making the intended compound, 1α,25-dihydroxycholecalciferol, under very mild conditions, whereby such side reactions as elimination of hydroxyl groups and rearrangement of double bonds can be prevented. In addition, hydroxyl groups need not particularly be protected and the intended compound can be obtained very efficiently without adopting complicated reaction or purification means.

In accordance with this invention, 1α,25-dihydroxycholecalciferol (I) is prepared by isomerizing cholesta-1,4,6-trien-3-on-25-ol (IX) in the presence of a basic catalyst to form cholesta-1,5,7-trien-3-on-25-ol (VIII), reducing the so formed compound with a metal hydride to form cholesta-1,5,7-trien-3β,25-diol (VII), reacting the so formed compound with a 1,2,4-triazoline-dione derivative represented by the following general formula (VI)

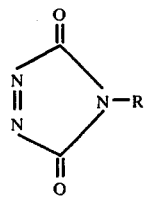

wherein R represents an organic residue, to form a 1,4-cyclic adduct represented by the following general formula (V)

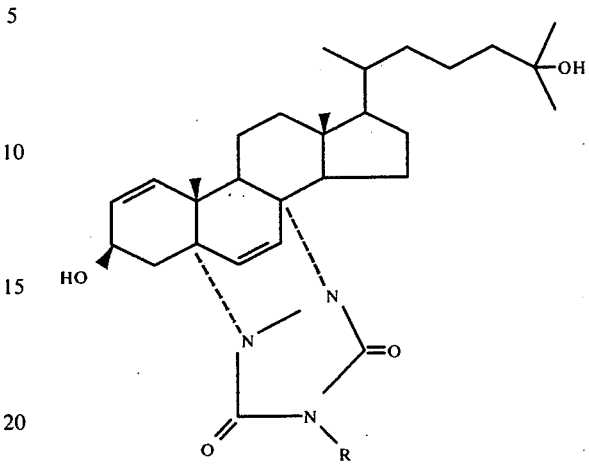

wherein R is as defined above, reacting the so formed compound with a peroxide to obtain a 1α,2α-epoxide compound represented by the following general formula (IV)

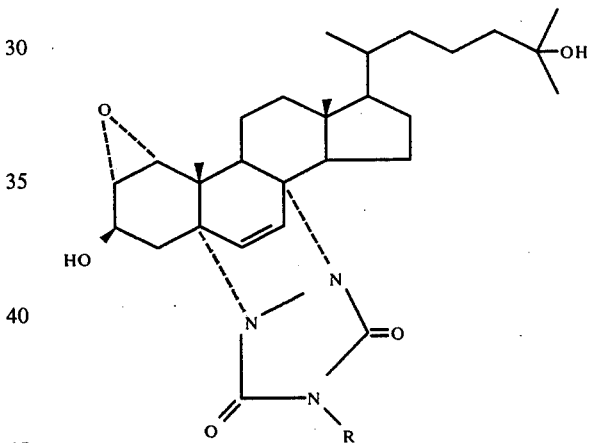

wherein R is as defined above, reducing the so formed compound with a metal hydride to form cholesta-5,7-diene-1α,3β,25-triol (III), irradiating the so formed compound with ultraviolet rays to form 1α,25-dihydroxyprevitamin $D_3$ (II), isomerizing the so formed previtamin $D_3$, and recovering 1α,25-hydroxycholecalciferol.

DETAILED DESCRIPTION OF THE PREFERRED EMBODIMENTS

The starting material for the process of this invention, namely, cholesta-1,4,6-trien-3-on-25-ol, was obtained from cholesterol as follows. Cholesterol was converted to cholesterol acetate by known procedures after which the cholesterol acetate was converted to 25-hydroxycholesterol acetate utilizing the procedures of A. Rotman and Y. Mazur (J. Chem. Soc., Chem. Comm., 1974, 15). The recovered 25-hydroxycholesterol acetate was hydrolyzed quantitatively with aqueous 5% KOH/MeOH to 25-hydroxycholesterol.

The 25-hydroxycholesterol was dissolved in dioxane and boiled with 2,3-dichloro-5,6-dicyanobenzo-quinone (DDQ) to obtain 25-hydroxycholesta-1,4-diene-3-one. This latter compound was subjected to dehydrogenation with chloroanil in the presence of the reduced derivative of DDQ-hydroquinone (2HDDQ) to obtain 25-hydroxy-cholesta-1,4,6-triene-3-one. Alternatively, 25-hydroxy-cholesta-1,4,6-trien-3-one can be obtained by DDQ oxidation of 25-hydroxycholesterol (J. J. Partridge et al., Helv. Chim. Acta 57, 764 (1974) which was converted from 6β-methoxy-25-hydroxy-3α,5-cyclo-5α-cholestane.

The cholesta 1,4,6-trien-3-on-25-ol (IX) is subjected to isomerization in the presence of a basic catalyst whereby the two double bonds located at $\Delta^{4,5}$ and $\Delta^{6,7}$ positions are isomerized to $\Delta^{5,6}$ and $\Delta^{7,8}$ positions respectively. Although any of the well known basic catalysts which promote such isomerization can be used the preferred catalysts are the alcoholates, such as methylates, ethylates and particularly potassium t-butoxide.

The isomerization is preferably carried out in a solvent which has a high dissolving power for the starting compound including, in general, organic solvents such s ethers, benzene type solvents and hydrocarbon solvents. Solvents such as ether (ethyl), isopropyl ether, tetrahydrofuran, dimethylsulfoxide, and tertiary butyl alcohol find ready application. Excellent results are obtained when, for example, dimethylsulfoxide as the solvent and potassium t-butoxide as the catalyst are used in combination for the isomerization reaction. In addition, it is desirable that the reaction be carried out in an atmosphere of inert gas such as argon or nitrogen.

The isomerization reaction can be carried out over a reasonably broad temperature range although the preferred range is from about 0° to about 20° C. Higher or lower temperatures may be used but find practical limits in their influence upon time of reaction, stability, or instability of reactants to certain temperatures.

The compound (VIII) is isolated from the reaction mixture according to a customary procedure, for example, by neutralizing the resulting reaction mixture liquid, extracting it, concentrating the extract and subjecting the concentrate to column chromatography or the like. Because of yield considerations, however, it is preferred that the reaction mixture be forwarded to the next step directly without isolation of the compound (VIII).

The compound (VII) is obtained by reducing compound (VIII) with a metal hydride. Metal hydrides suitable for such reduction, are, for example, lithium aluminum hydride, metal boron hydrides such as sodium boron hydride, potassium boron hydride or lithium boron hydrides, sodium borohydride and calcium borohydride. It is preferred that the reduction reaction be carried out in a solvent, and use of an ether type solvent such as ether, tetrahydrofuran, 1,2-dimethoxyethane, diglyme (diethylene glycol dimethyl ether) and the like. When sodium borohydride or calcium borohydride is used as the metal hydride, a hydroxyl group-containing solvent such as water, methanol and ethanol can be used. The reaction temperature is suitably chosen within a range of from lowered temperatures to elevated temperatures. The preferred temperature range for the reaction is from about 0° to about 20° C.

Isolation of the compound (VII) from the reaction mixture can be accomplished according to customary methods, for example, by neutralizing and extracting the reaction mixture liquid, concentrating the extract and subjecting the concentrate to column chromatography or the like. It is possible to forward the reaction mixture directly to the subsequent step without isolation of the compound (VII).

The compound (V) is prepared by reacting compound (VII) with compound (VI). It is preferred that the reaction be carried out in a solvent that does not participate in the reaction. In general, use of organic solvents such as ethers, benzene-type solvents and hydrocarbon solvents is preferred. Specific examples of preferred solvents are benzene, tetrahydrofuran and methylene chloride. The reaction temperature is suitably chosen within a range of from lower temperatures to elevated reflux temperatures.

In the 1,2,4-triazoline-3,5-dione derivative represented by the general formula (VI), any of organic residues inactive to the reaction can be used as R. With the preferred solvents for the reaction it is generally preferred that R be a monocyclic aromatic residue or a lower alkyl group. Specific examples of such preferred organic residues are phenyl, mono-substituted phenyl, methyl and ethyl groups.

Isolation of the compound (V) from the reaction mixture is performed by concentrating the reaction mixture, extracting the concentrate with a solvent such as benzene or methylene chloride, and subjecting the extract to column chromatography.

The compound (IV) is prepared by reacting compound (V) with a peroxide. An organic peracid is preferably used as the peroxide. As the peracid, there can be employed, aromatic peracids such as perbenzoic acid and m-chloroperbenzoic acid and aliphatic peracids such as permaleic acid, peracetic acid and pertrifluoroacetic acid. It is preferred that the reaction be carried out in a solvent, for example, ethers, such as ethyl ether and tetrahydrofuran chlorinated hydrocarbon solvents, such as chloroform and methylene chloride, alkyl esters of organic acids such as ethyl acetate, and fatty acids such as acetic acid the peroxide being present in an amount of about 1 to 5 moles per mole of compound V. In view of the inactivity toward the peroxide used and the dissolving power toward the reactants, use of hydrocarbon solvents such as methylene chloride and chloroform is especially preferred. The reaction temperature is chosen within a range of from lowered temperatures to elevated temperatures depending on the kind of the peroxide used.

The compound (III) is obtained by reducing compound (IV) with a metal hydride. The metal hydrides which are preferably employed are lithium aluminum hydride and lithium borohydride. The reaction is normally carried out in a solvent, such as the ether type solvents, for example, ethyl ether, tetrahydrofuran, 1,2-dimethoxyethane and diglyme, which are especially preferred. The reaction temperature is chosen suitably within a range of from lowered temperatures to elevated temperatures, for example from about 50° to about 150° C.

Isolation of the compound (III) from the reaction mixture is performed according to customary methods, e.g., by decomposing the excessive metal hydride, extracting the reaction mixture, concentrating the extract and subjecting the concentrate to column chromatography or the like.

Compound (III) is then irradiated with ultraviolet rays to form compound (II) in which the ring B of the steroid skeleton is cleaved. The irradiation is generally conducted in a solvent. Hydrocarbon-type solvents, ether-type solvents and alcohols can be readily employed. Examples of preferable hydrocarbon-type solvents are saturated hydrocarbon solvents, especially those having a low boiling point, such as hexane and octane. Ether type solvents which are preferably employed are the low-boiling-point saturated ethers, such as ethyl ether and tetrahydrofuran and the preferable alcohols are the lower alcohols such as methanol and ethanol. It is preferred that the reaction be carried out at a temperature approximating room temperature and in an atmosphere of an inert gas such as argon. The time for irradiation of ultraviolet rays varies depending upon the intensity of the ultraviolet source lamp and the reaction scale. In general, the irradiation time is within a range of from scores of seconds to several hours.

Compound (II) is isolated from the reaction mixture according to customary methods, for example, by concentrating the reaction mixture and subjecting the concentrate to chromatography or the like. It is possible to forward the reaction mixture to the subsequent step directly without isolation of the compound (II).

The compound (I) is formed by isomerizing the compound (II) with thermal equilibrium being established between the compound (II) and the desired end compound (I). The isomerization reaction is carried out in accordance with known and customary methods, for example, by allowing the compound (II) to stand for a period in the dark at room temperature, or by heating it in a solvent. Any solvents which are inactive to the reaction, e.g., hydrocarbon-type solvents, ether-type solvents and alcohols can be used. Preferred solvents are those having a low boiling point and a high dissolving power for the compound (II), such as hexane, isooctane, toluene, ether and tetrahydrofuran. Depending upon the reaction conditions the reaction time may range from several hours to several weeks. When compound (II) is allowed to stand in the dark, it is preferred that the reaction continue for several weeks. When the reaction is carried out under heating and refluxing, it is preferred that the reaction continue only for several hours.

Isolation of the end product, $1\alpha,25$-dihydroxycholecalciferol from the reaction mixture is accomplished by known and customary purification means such as extraction, recrystallization, column chromatography and partition chromatography. Column chromatography using a column packed with Sephadex (manufactured by Pharmacia Fine Chemicals) is especially effective. Unisomerized compound (II) is also obtained in the separation procedure and this unisomerized compound (II) can be recycled for further isomerization after recovery.

Each of intermediate compounds (VIII), (VII), (V), (IV), (III) and (II) formed in the process of this invention are novel and form another aspect of this invention.

A more complete understanding of the invention can be obtained from reference to the following specific examples which are included for purposes of illustration only and are not intended to be limiting.

EXAMPLE 1

1. Preparation of cholesta-1,5,7-trien-3-on-25-ol.

A reaction vessel was charged with 125 ml of dry dimethylsulfoxide and 2.5 g of cholesta-1,4,6-trien-3-on-25-ol was suspended in the dimethylsulfoxide. The suspension was heated, and 10 ml of dry ether was added to the resulting milky suspension to obtain a transparent solution. The reaction vessel was filled with dry argon gas. Powdery potassium t-butoxide prepared from 1.25 g potassium and 50 ml of butanol was added at one time to the solution under ice cooling and with violent agitation. The reaction mixture liquid was violently agitated for 12 minutes and was then poured into ice water saturated with carbon dioxide gas, which was prepared by adding dry ice to water. The mixture was then extracted with 600 ml of ether cooled to 0° to 5° C. The extract was promptly washed with cooled water saturated with a large quantity of carbon dioxide until the washing liquid became neutral, and the ether was then distilled off to obtain crude cholesta-1,5,7-trien-3-on-25-ol.

2. Preparation of cholesta-1,5,7-triene-$3\beta,25$-diol.

100 ml of an ethanol solution containing 2.5 g of sodium borohydride was added dropwise under agitation to 110 ml of methanol containing 4.9 g of calcium chloride, which was cooled below $-10°$ C. The mixture was agitated for 20 minutes while maintaining the temperature at about $-10°$ C. Then, 100 ml of the ether solution containing crude cholesta-1,5,7-trien-3-on-25-ol, which was prepared in (1.) above, was added dropwise to the above mixture. The reaction mixture was further agitated at $-10°$ C. for 1 hour and at 0° C. for 1 hour, and was then neutralized with 10% acetic acid after which the solvent was distilled off under reduced pressure. The residue was extracted with methylene chloride and the extract was washed with water and dried with magnesium sulfate. Methylene chloride was distilled off to obtain crude cholesta-1,5,7-triene-$3\beta,25$-diol (about 1 g). 3. Preparation of 1,4-cyclized adduct of cholesta-1,5,7-triene-$3\beta,25$-diol and 4-phenyl-1,2,4-triazoline-3,5-dione.

About 500 mg of 4-phenyl-1,2,4-triazoline-3,5-dione was added little by little under agitation to 50 ml of a methylene chloride solution containing the crude cholesta-1,5,7-triene-$3\beta,25$-diol (about 1 g) obtained in (2.) above, until the methylene chloride solution became red. The solution was agitated at room temperature for 1 hour, and methylene chloride was distilled off and the residue was subjected to column chromatography using a column packed with 200 g of alumina. A chloroform effluent fraction was collected and recrystallized from methanol to obtain 1.4 g (the overall yield being 38.1%) of a cyclic adduct of cholesta-1,5,7-triene-$3\beta,25$-diol and 4-phenyl-1,2,4-triazoline-3,5-dione having a melting point of 159° to 160° C.

Elementary Analysis Values as $C_{35}H_{47}O_4N_3 \cdot \frac{1}{2}H_2O$:
Calculated: C = 72.13%, H = 8.30%, N = 7.21%;
Found: C = 72.06%, H = 8.15%, N = 7.45%.

EXAMPLE 2

197.3 mg of the 1,4-cyclic adduct obtained in Example 1 was dissolved in 5 ml of chloroform and 237 mg of m-chloroperbenzoic acid was added to the solution after which the mixture was agitated for 40 hours at room temperature. The reaction mixture liquid was diluted with chloroform, washed with a 10% aqueous solution of potassium carbonate, dried with anydrous magnesium sulfate, and the solvent was distilled off under reduced pressure. The residue was subjected to silica gel column chromatography. A $1\beta,2\beta$-epoxide of the 1,4-cyclic adduct melting at 159° to 160.5° C. was recovered from a fraction primarily eluted with methanol-containing ether, and from the subsequent fraction was obtained 68.3 mg of a $1\alpha,2\alpha$-epoxide of the 1,4-cyclic adduct having a melting point of 162° to 163.5° C. (as measured with respect to a product recrystallized from methanol).

Elementary Analysis Values as $C_{35}H_{47}O_5N_3 \cdot \frac{1}{2}H_2O$:
Calculated: C = 70.21%, H = 8.03%, N = 7.02%;
Found: C = 70.02%, H = 7.83%, N = 7.03%.

EXAMPLE 3

Preparation of cholesta-5,7-diene-1α,3β,25-triol.

140.3 g of the 1α,2α-epoxide of the 1,4-cyclic adduct of cholesta-1,5,7-triene-3β,25-diol and 4-phenyl-1,2,4-triazoline-3,5-dione obtained in Example 2 was dissolved in 15 ml of tetrahydrofuran, and 142 mg of lithium aluminum hydride was added little by little to the solution under agitation. Then, the mixture was mildly refluxed and boiled for 1 hour and cooled, and 20 ml of tetrahydrofuran was added to the reaction mixture. A saturated aqueous solution of Glauber salt was added to the reaction mixture until generation of bubbles was stopped, whereby excessive lithium aluminum hydride was decomposed. The reaction mixture was then filtered, and the residue was washed 3 times with 10 ml of tetrahydrofuran. The organic solvent layer was dried and the solvent was distilled off. The residue was purified by using a column packed with 20 g of Sephadex LH 20, and a fraction eluted by chloroform-hexane (65 : 35 V/V ratio) was collected and recrystallized from ether-hexane to obtain 49.9 mg of cholesta-5,7-diene-1α,3β,25-triol in the form of needles melting at 149° to 152° C.

Mass Spectrum: m/e 416(M⁺), 398, 380, 362
UV Spectrum: λ max/Et₂O 263, 272, 282, 294 mμ

EXAMPLE 4

Preparation of 1α,25-dihydroxyprevitamin D₃

A solution of 31.5 mg of cholesta-5,7-diene-1α,3β,25-triol in 380 ml of ether was exposed for 1 minute to ultraviolet rays through a Vycor filter in an argon gas atmosphere by using a 400-W high pressure mercury lamp (manufactured by Toshiba). The solvent was distilled off at room temperature under reduced pressure, and the residue was subjected to column chromatography using a column packed with 20 g of Sephadex LH-20. From a fraction primarily eluted by chloroform-hexane (65 : 35 V/V ratio) was obtained 10.5 mg of oily 1α,25-dihydroxyprevitamin D₃ (having a maximum ultraviolet absorption at 260 mμ in an ether solution), and from the subsequent fraction was recovered 14.3 mg of cholesta-5,7-diene-1α,3β,25-triol. When this compound was exposed to ultraviolet rays in the same manner as above, 4.5 mg of 1α,25-dihydroxyprevitamin D₃ was obtained.

EXAMPLE 5

Preparation of 1α,25-dihydroxycholecalciferol.

The 1α,25-dihydroxyprevitamin D₃ obtained in Example 4 above was dissolved in 100 ml of ether, and the solution was allowed to stand at room temperature in the dark in a vessel filled with argon gas for 2 weeks, during which the position of the maximum ultraviolet absorption was shifted from 260 mμ to 264 mμ and the absorption intensity was increased to 1.6 times the initial intensity. The solvent was distilled off under reduced pressure and the residue was subjected to chromatography using a column packed with 10 g of Sephadex LH-20. From a fraction eluted by chloroform-hexane (65 : 35 V/V ratio) was obtained 9.3 mg of oily 1α,25-dihydroxycholecalciferol having a melting point of 95° to 99° C. (as measured with respect to a needle crystal recrystallized from chloroform). Mass Spectrum: m/e 416(M⁺), 398, 380, 362, 269, 251, 152, 134

UV Spectrum: λ max/EtOH 264 mμ

It will be apparent to one of ordinary skill in the art that in the foregoing Examples other solvents and reactants, as well as reaction conditions compatible with such solvents and reactants, such as those set forth in the foregoing specification, can be employed with comparable results.

What is claimed is:
1. Cholesta-1,5,7-trien-3-on-25-ol.
2. Cholesta-1,5,7-trien-3β,25-diol.
3. A compound having the formula

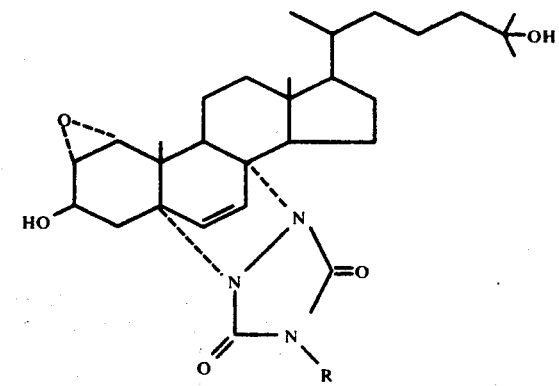

where R represents an alkyl, aryl or mono-substituted aryl group.
4. Cholesta-5,7-diene-1α,3β,25-triol.
5. 1α,25-dihydroxyprevitamin D₃.

* * * * *